(12) United States Patent
Odoi

(10) Patent No.: US 8,377,021 B2
(45) Date of Patent: Feb. 19, 2013

(54) ABSORBENT ARTICLE

(75) Inventor: Haruko Odoi, Sakura (JP)

(73) Assignee: DAIO Paper Corporation, Shikokuchuo-shi, Ehime (JP)

( * ) Notice: Subject to any disclaimer, the term of this patent is extended or adjusted under 35 U.S.C. 154(b) by 300 days.

(21) Appl. No.: 12/745,647

(22) PCT Filed: Nov. 26, 2008

(86) PCT No.: PCT/JP2008/071411
§ 371 (c)(1),
(2), (4) Date: Jun. 21, 2010

(87) PCT Pub. No.: WO2009/069635
PCT Pub. Date: Jun. 4, 2009

(65) Prior Publication Data
US 2010/0305539 A1      Dec. 2, 2010

(30) Foreign Application Priority Data
Nov. 30, 2007 (JP) .................. 2007-311034

(51) Int. Cl.
*A61F 13/15* (2006.01)
(52) U.S. Cl. ......... 604/385.01; 604/385.28; 604/385.29; 604/385.3; 604/385.25

(58) Field of Classification Search ............. 604/385.25, 604/385.28, 385.29, 385.3, 385.01
See application file for complete search history.

(56) References Cited

U.S. PATENT DOCUMENTS
6,475,200 B2 * 11/2002 Mizutani et al. ......... 604/385.01

FOREIGN PATENT DOCUMENTS
| JP | 61-014029 | 1/1986 |
|----|-----------|--------|
| JP | 03-018824 | 2/1991 |
| JP | 2003-111792 | 4/2003 |
| JP | 2003-275240 | 9/2003 |
| JP | 2004-049696 | 2/2004 |

* cited by examiner

*Primary Examiner* — Jacqueline F. Stephens
(74) *Attorney, Agent, or Firm* — Jordan and Hamburg LLP

(57) ABSTRACT

Winkles are prevented from being generated in the flap portion to reduce an uncomfortable feeling and friction. In a sanitary napkin including an absorber interposed between a liquid-permeable top sheet and a liquid-impermeable back sheet and a flap portion surrounding the absorber without including the absorber, the flap portions at least in a front area and a back area of the sanitary napkin each have an outer shape of a wave-like line composed of convex curves and concave curves in which the direction of a line tangent to the outline of the flap portion is continuously changed; the width of the absorber gradually narrows in each of the front side area and the back side area in such a manner that lines incline toward each other to form a convex curve; and the wave-like line is formed along each of the inclining lines.

4 Claims, 10 Drawing Sheets

ABSORBENT ARTICLE

BACKGROUND OF THE INVENTION

The present invention relates to an absorbent article such as a sanitary napkin, a pantiliner, or an incontinence pad for absorbing menstrual blood, vaginal discharge, and the like, and, specifically, relates to an absorbent article in which an uncomfortable feeling when it is worn is reduced by preventing wrinkles of its flap portion from being generated.

As absorbent articles for sanitary napkins, pantiliners, vaginal discharge sheets, incontinence pads, and the like, conventionally known is, for example, as shown in FIG. 8, an absorbent article N that includes an absorber 52 formed of, for example, cotton-like pulp interposed between a back sheet 50 formed of, for example, a polyethylene sheet or a polyethylene laminated nonwoven fabric and a liquid-permeable top sheet 51 formed of, for example, a nonwoven fabric or a porous plastic sheet and also includes side nonwoven fabrics 53 respectively disposed on both sides of the top surface along the longitudinal direction and a flap portion at the circumference of the absorber 52. The flap portion is constituted by bonding the back sheet 50 and the top sheet 51 or the side nonwoven fabrics 53 and does not include the absorber 52.

In such a type of the absorbent article N, since the absorber 52 is substantially square or 8-shaped, the outline is also substantially square, oval, or 8-shaped, and, usually, its front end and back end are each shaped in a simple arc-shaped curve in order to soften the contact with the skin (for example, see herein referenced Patent Documents 1 and 2).

When the absorbent article N is fixed to a undergarment 20, as shown in FIG. 9, the absorbent article N is put at an appropriate local portion of the undergarment 20, and both the wing-like flaps W, W that protrude sideward are taken out from the undergarment, folded back along folding lines RL, RL, and attached to the outer surface of the crotch of the undergarment 20 so as to wrap around the crotch portion of the undergarment. The patent documents herein referred to are:

[Patent Document 1] JP-A-2003-275240
[Patent Document 2] JP-A-2004-49696

SUMMARY OF INVENTION

However, in such an absorbent article N, as shown in FIG. 10, for example, when the legs of a subject being seated are located at positions LF, both sides regions (shown by diagonal lines) of areas of the flap portion near the front of the absorbent article are pushed by the inner sides of the legs, and thereby wrinkles are formed in those areas. If a pushing pressure is further applied, the wrinkles develop from the both sides toward the inside, which causes wrinkles of the entire front area of the flap portion and turning over of the flap portion at front areas thereof. In particular, as described above, in the conventional absorbent article N having a substantially square, oval, or 8-shaped shape as a whole, the pushing pressures from the inner sides of the legs tends to be applied to both sides of the front area of the flap portion, which tends to cause wrinkles in the flap portion.

In addition, since the legs of a subject being seated are located at positions LF, wrinkles are generated in the shorts itself. Therefore, the flap portion is required to be bent integrally with the wrinkles generated in the shorts itself and to return flat along the shorts without the wrinkles remaining when the wrinkles of the shorts are smoothened. However, in the conventional absorbent article N, as described above, since the front end of the flap portion is formed into a simple arc-shaped curve, the flap portion is bent or turned over by application thereto of the pushing pressure from the inner sides of the legs, and the bending and the turning of the flap portion remain even after the wrinkles of the shorts are smoothened.

The wrinkles, bending, and turning generated in the flap portion cause problems such that they impinge on the body to cause an uncomfortable feeling or that friction between the skin and the wrinkles is readily caused.

On the other hand, for example, while the wearer is walking, as shown in FIG. 10, the wearer's legs are located at positions LB. In this case, wrinkles, bending, and turning are generated in the back area of the flap portion, similar to the hereinabove description with respect to the front area of the flap portion, which causes an uncomfortable feeling and friction.

Accordingly, a main object of the present invention is to provide an absorbent article in which wrinkles are prevented from being generated in the flap portion to mitigate any uncomfortable feeling and friction when the absorbent article is worn.

In order to solve the above-mentioned problems, the invention according to a first aspect thereof provides an absorbent article including a liquid-permeable top sheet, a liquid-impermeable back sheet, an absorber interposed therebetween, and a flap portion surrounding the absorber without including the absorber, wherein the flap portion has an outer shape, at least in a front area and a back area of the absorbent article, of a wave-like line composed of convex curves and concave curves in which the direction of a line tangent to the outline of the flap portion is continuously changed; the width of the absorber gradually narrows in each of the front area and the back area in such a manner that lines incline toward each other to form a convex curve; and the wave-like line is formed along each of the inclining lines.

In the first aspect of the invention, the outline of the flap portion at least in the front area and the back area of the absorbent article is the wave-like line composed of convex curves and concave curves in which the direction of a line tangent to the outline of the flap portion is continuously changed; even if both sides of the flap portion in the front area and the back area are pushed by the inner sides of the legs, the wave-like line functions such that the pushing pressure is gradually applied or is dissipated and that wrinkles generated in the both side areas of the flap portion are prevented from developing toward the inside. And also, since the outline of the flap portion is formed by the wave-like line, the wave-like line also functions against force generated by expansion and contraction of shorts itself by movement of the legs such that the pushing pressure is gradually applied or is dissipated and that bending and turning of the flap portion are prevented from being generated. Consequently, wrinkles of the flap portion are prevented from being generated, and thereby an uncomfortable feeling and friction when the absorbent article is worn are reduced.

In addition, in the front area and the back area of the absorbent article, the width of the absorber gradually narrows in such a manner that lines incline toward each other to form a convex curve, and the wave-like line is formed along each of the inclining lines. That is, since the absorber has a shape in which portions that would otherwise be brought into contact with the legs are eliminated and the wave-like line is formed along the shape, the pushing pressure from the inner sides of the legs is reduced in both sides of the front area and the back area of the absorbent article, reducing the generation of wrinkles in the flap portion.

The second aspect of the present invention provides the absorbent article of the first aspect, wherein the flap portion in the front area and the back area of the absorbent article is formed such that a flap width from the edge of the absorber to the outline is relatively large at the central end extremities of the absorbent article and that a flap width from the edge of the absorber to the outline is relatively small at the wave-like line region formed along the inclining lines on both sides.

In the second aspect of the invention, the absorbent article is constituted such that front leakage and back leakage of body fluid are prevented by the flap portion having a large width at the central end extremities, which are not brought into contact with the legs of a subject being seated or walking, of the absorbent article. At the same time, wrinkles and twists are prevented from being generated in the flap portion by reducing the width of the flap portion at the regions where the wave-like lines that are brought into contact with upper extremities of the legs are formed.

The third aspect of the present invention provides the absorbent article according to the first or second aspect, wherein the flap portion in the front area and the back area of the absorbent article has an outer shape, i.e., outline, composed of a convex curve with a relatively large curvature at the central end extremities of the absorbent article and curves being combination of concave curves and convex curves with relatively small curvatures at the wave-like line regions formed along the inclining lines on both sides.

In the third aspect of the invention, the curvatures of the convex curves and concave curves are varied in each flap portion, for dealing with pushing pressures in various directions from the inner side of the legs and also for dealing with wrinkles in various angles generated in shorts.

According to the present invention as described in detail above, since wrinkles can be prevented from being generated in the flap portion, an uncomfortable feeling and friction when the absorbent article is worn can be reduced.

DETAILED DESCRIPTION OF THE INVENTION

Figure 1:
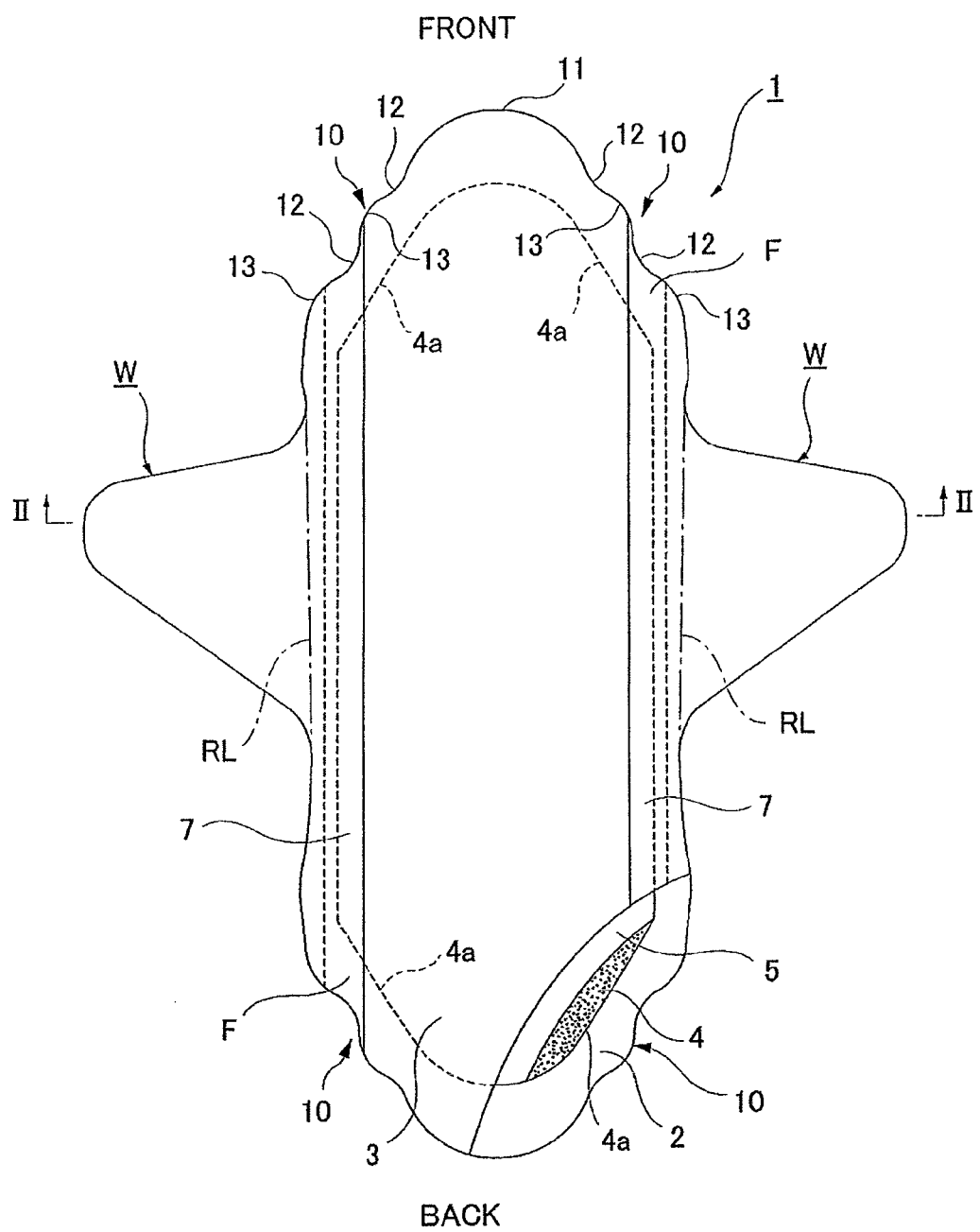
FIG. 1 is a partially broken development view of a sanitary napkin 1 according to the present invention.
Figure 2:
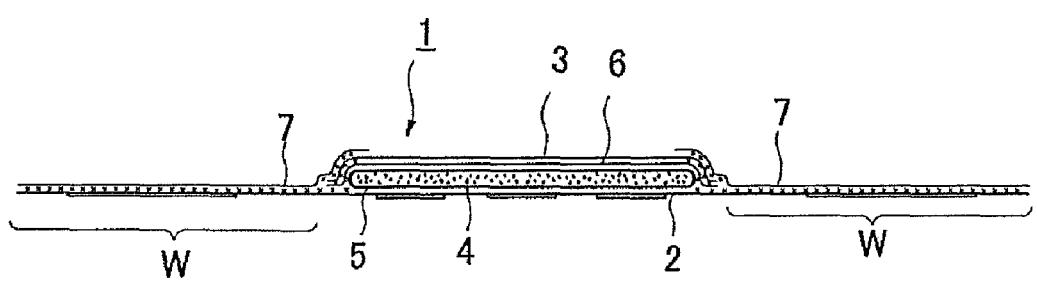
FIG. 2 is a fragmentary view taken along the II-II line in FIG. 1.

Embodiments of the present invention will be described in detail below with reference to drawings. FIG. 1 is a partially broken development view of a sanitary napkin 1 according to the present invention, and FIG. 2 is a fragmentary view taken along the II-II line in FIG. 1.

The sanitary napkin 1 is constituted of a liquid-impermeable back sheet 2 composed of, for example, a polyethylene sheet or a polypropylene sheet; a liquid-permeable top sheet 3 that allows menstrual blood, vaginal discharge, or the like to rapidly permeate; an absorber 4 made of, for example, cotton-like pulp or synthetic pulp and interposed between the sheets 2 and 3; crepe paper 5 surrounding the absorber 4 for maintaining the shape of the absorber 4 and increasing diffusing ability; and side nonwoven fabrics 7, 7 respectively disposed at both sides of the top face along the longitudinal direction. The outer edges of the liquid-impermeable back sheet 2 and the liquid-permeable top sheet 3 are bonded to each other at the upper and lower ends in the circumference of the absorber 4 with an adhesive such as hot melt or by adhesion means such as heat sealing, and, at both side edges, the liquid-impermeable back sheet 2 protruding sidewards beyond the absorber 4 and each side nonwoven fabric 7 are bonded to each other with an adhesive such as hot melt or by adhesion means such as heat sealing to form a flap portion F at the periphery of the sanitary napkin, not having the absorber 4.

The structure of the sanitary napkin 1 will be further described in detail below.

As the liquid-impermeable back sheet 2, a sheet material having at least a waterproof property, for example, an olefin-based resin sheet such as polyethylene or polypropylene, is used. In addition, a laminated nonwoven fabric in which a nonwoven fabric is laminated to, for example, a polyethylene sheet or a nonwoven sheet provided with a waterproof film for ensuring a substantial liquid-impermeable property (in such a case, the waterproof film and the nonwoven fabric constitute a liquid-impermeable back sheet) can be used. Recently, from the viewpoint of preventing a damp or humid feel, a material having moisture permeability tends to be used. Such a waterproof and moisture-permeable sheet material is a micro-porous sheet that is prepared by melt-kneading an inorganic filler in an olefin-based resin such as polyethylene or polypropylene and forming it into a sheet and then uniaxially or biaxially stretching the sheet. In particular, in the present invention, in order to assure that the flap portion F, which is described in detail in a latter part, conform to the shorts S, the back sheet 2 is preferably made of a material having high flexibility, such as a film.

The liquid-permeable top sheet 3 is preferably made of porous or nonporous nonwoven fabric or a porous plastic sheet. Examples of a fibrous base material constituting the nonwoven fabric include, in addition to synthetic fiber such as olefin-based (such as polyethylene or polypropylene), polyester-based, and polyamide-based synthetic fiber, recycled fiber such as rayon or cupra and natural fiber such as cotton, and the nonwoven fabric prepared by any suitable processing method such as spunlacing, spunbonding, thermal bonding, meltblowing, or needle punching can be used. Among these processing methods, spunlacing provides nonwoven fabric excellent in flexibility and drape property, and thermal bonding provides nonwoven fabric excellent in bulk and softness.

The absorber 4 interposed between the liquid-impermeable back sheet 2 and the liquid-permeable top sheet 3 is constituted of, for example, fluff-like pulp and a water-absorbing polymer. The water-absorbing polymer, for example, in a form of granular powder, is mixed in pulp constituting the absorber. Examples of the pulp include those composed of cellulose fiber such as chemical pulp made from wood and melting pulp and those composed of artificial cellulose fiber such as rayon and acetate. Softwood pulp has a longer fiber length than that of hardwood pulp and is preferably used in the light of function and cost performance. When crepe paper 5 surrounding the absorber 4 as in this embodiment is used, the crepe paper 5 is accordingly interposed between the liquid-permeable top sheet 3 and the absorber 4. Consequently, the crepe paper 5, which is excellent in absorbability, allows rapid diffusion of body fluid and prevents returning back of menstrual blood and the like. In particular, as described in detail in a latter part, since it is an object of the present invention to reduce an uncomfortable feeling when the napkin is worn, the thickness of the absorber 4 is preferably in a range of about 0.5 to 2 mm, and the absorber 4 is preferably produced as an air-laid absorber of pile pulp so as to be highly flexible. Furthermore, although it is not shown in the drawings, the absorber 4 may have a structure with an elevation in its center, i.e., a portion corresponding to a blood discharge opening is thick.

Furthermore, the sanitary napkin 1 is provided with side nonwoven fabrics 7, 7 at both sides of the top surface along the longitudinal direction for approximately the entire length of the napkin 1. The side nonwoven fabrics 7, 7 partially extend sideward and form the wing-like flaps W, W together with parts of the liquid-impermeable back sheet 2 similarly extending sideward. The wing-like flap W will be described in detail below.

The side nonwoven fabric 7 is formed of a water repellency-treated nonwoven fabric or hydrophilicity-treated nonwoven fabric, according to an important function. For example, when a function of preventing infiltration of menstrual blood, vaginal discharge, or the like or a function increasing texture is emphasized, it is desirable to use a nonwoven fabric provided with water repellency by being coated with, for example, a silicon-based, paraffin-based, alkyl chromic chloride-based water repellent agent. When absorbability of the wing-like flaps W, W for menstrual blood or the like is emphasized, used is a hydrophilicity-treated nonwoven fabric that is imparted with the hydrophilicity, applying capillarity, by making the synthetic fiber swollen or porous with the methods such as, polymerization in the presence of a compound having hydrophilic group such as an oxidation product of polyethylene glycol during a process of producing the synthetic fiber, or treating a surface with a metal salt such as stannic chloride for partially dissolving and making the surface porous and depositing a metal hydroxide.

In the present invention, in particular, the outer shape of the flap portion F at least in the front area and the back area of the sanitary napkin 1 is a wave-like line 10 composed of convex curves 11 and 13 and concave curves 12 in which the direction of a line tangent to the outline of the flap portion F is continuously changed. The width of the absorber 4 gradually narrows in both the front area and the back area of the sanitary napkin 1 in such a manner that lines incline toward each other to form a convex curve, and the wave-like line 10 is formed along the inclining line 4a.

Figure 4:
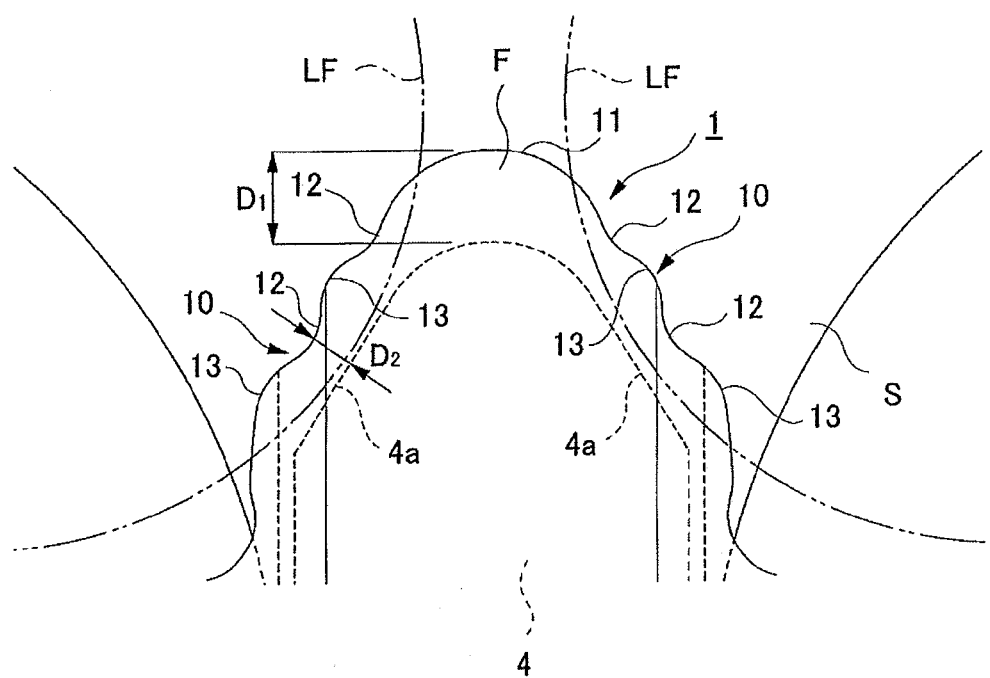
FIG. 4 is an enlarged view of the front side area of the sanitary napkin 1 in FIG. 3.

In further detail, as shown in FIG. 4, in the front area and the back area of the sanitary napkin 1, the outer shape of the flap portion F is a convex curve 11 having a relatively large curvature at the central portion in the width direction (central end extremity) of the sanitary napkin 1, and the wave-like line 10 formed along each of the inclining lines 4a on both sides is a wave-like curve composed of the convex curves 13 and the concave curves 12 alternately arranged so that the direction of a line tangent to the outline of the flap portion F is continuously varied with respect to a straight line parallel to the inclining line 4a of the absorber 4. In such a case, desirably, the convex curve 11 arranged at the central end extremity is a curve having a relatively large curvature of radius of 20 to 30 mm, and the wave-like line 10 portions formed along the inclining line 4a on both sides are each composed of concave curves 12 and convex curves 13 having a relatively small curvature of radius of 10 to 15 mm.

Figure 3:
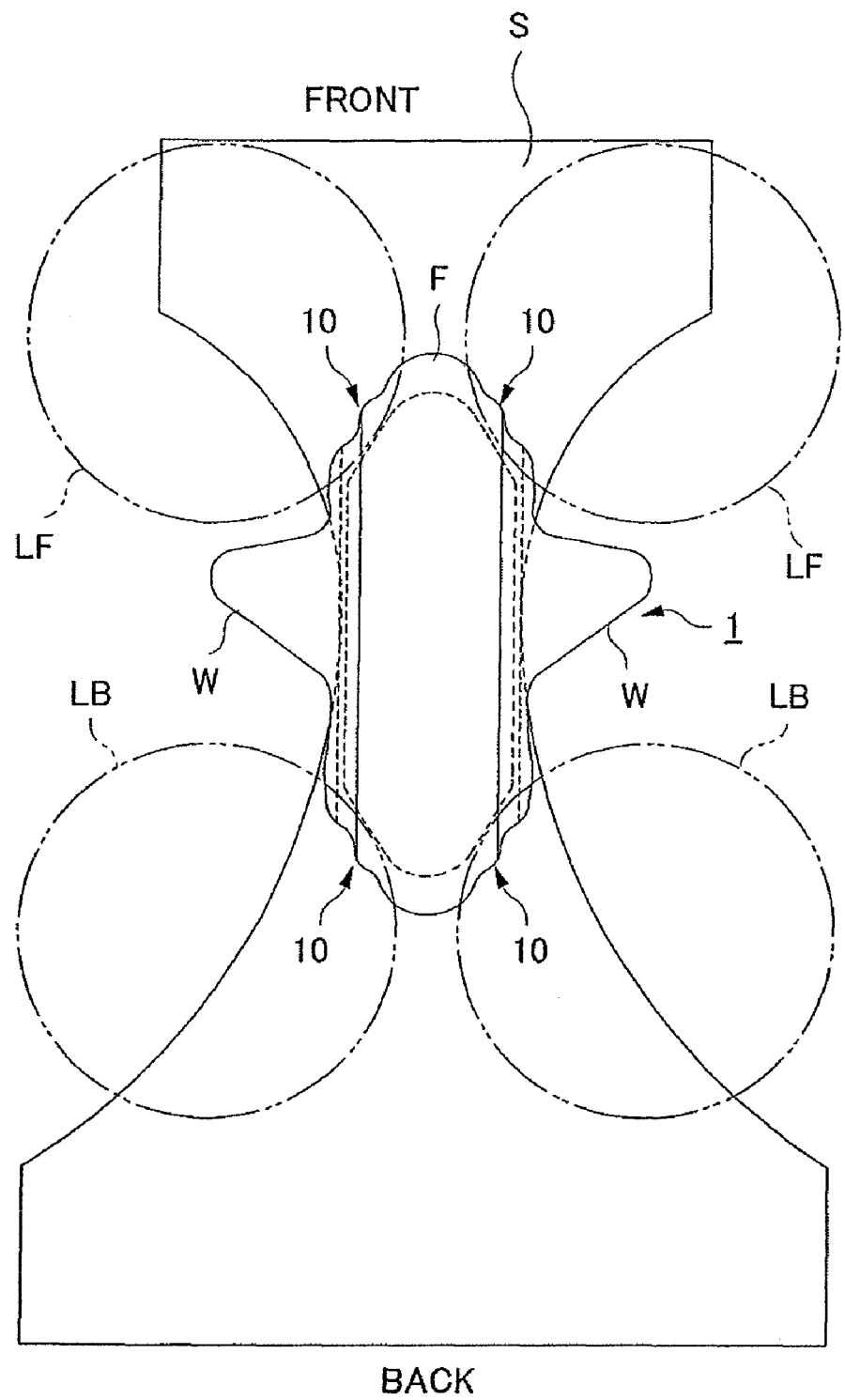
FIG. 3 is a development view of shorts showing positions of the legs with respect to the sanitary napkin 1.

As shown in FIG. 3, for example, the legs when a subject is seated are located at positions LF, LF with respect to the shorts S. In such a case, pushing pressure from the insides of the legs is applied to both sides of the front area of the flap portion F. However, in the sanitary napkin 1, since the wave-like line 10 is formed in the front area and the back area, the pushing pressure is gradually applied to the flap portion outline on the both sides (the points of application of force are intermittent) due to the concave curves 12 and the convex curves 11 and 13 of the wave-like line and the force is dissipated by the curves, preventing wrinkles from being formed in the flap portion F. In addition, even if wrinkles are generated, the range of the wrinkles is limited to the convex curves portions and thus do not propagate to the inside, whereby wrinkles are prevented from developing to the inside of the flap portion.

In addition, since the legs when a subject is seated are located at the positions at LF, LF, expansion and contraction are caused in the shorts S itself in portions thereof surrounding the legs, but compressive force or tensile force by friction caused by the expansion and contraction of the shorts S is gradually applied to the napkin 1 due to the concave curves 12 and the convex curves 11 and 13 of the wave-like line and is dissipated by the curves, which prevents generation of wrinkles in the flap portion F.

Furthermore, as shown in FIG. 4, in the sanitary napkin 1, the flap portion F in the front side area and the back side area is formed such that a flap width D1 from the edge of the absorber 4 to the outline is relatively large at the central end extremity of the sanitary napkin 1 and that a flap width D2 from the edge of the absorber 4 to the outline is relatively small at the region where the wave-like line 10 is formed along each of the inclining lines 4a on both sides. Front leakage of body fluid is prevented by the front central end extremity, which is not brought into contact with the legs even when a subject is seated or walking, of the sanitary napkin 1. And also, the structure prevents wrinkles and twists being generated in the flap portion F in the portions of the wave-like lines 10, which are brought into contact with the upper extremities of the legs.

Figure 5:
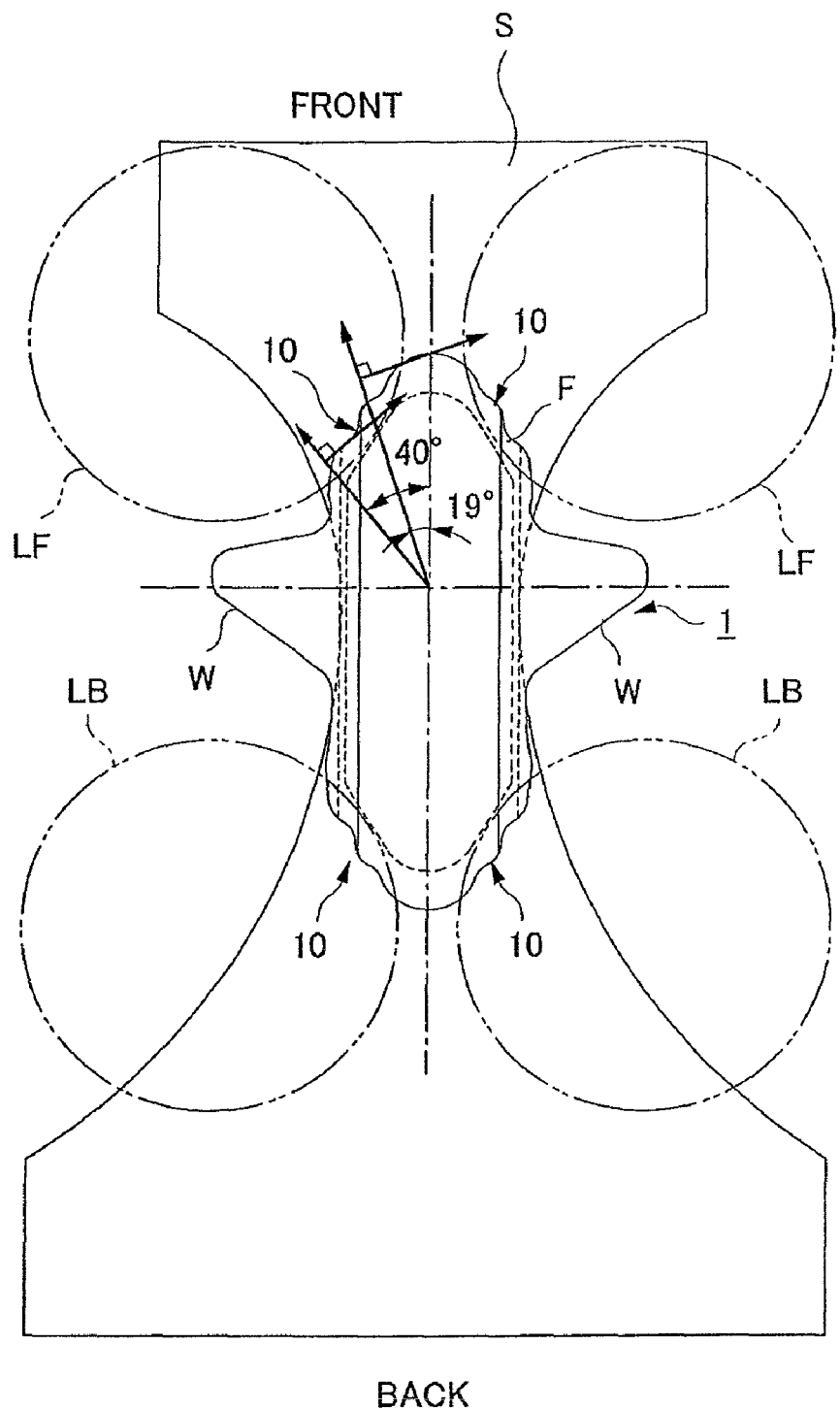
FIG. 5 is a development view of shorts for describing directions of wrinkles caused by movement of the shorts.
Figure 6:
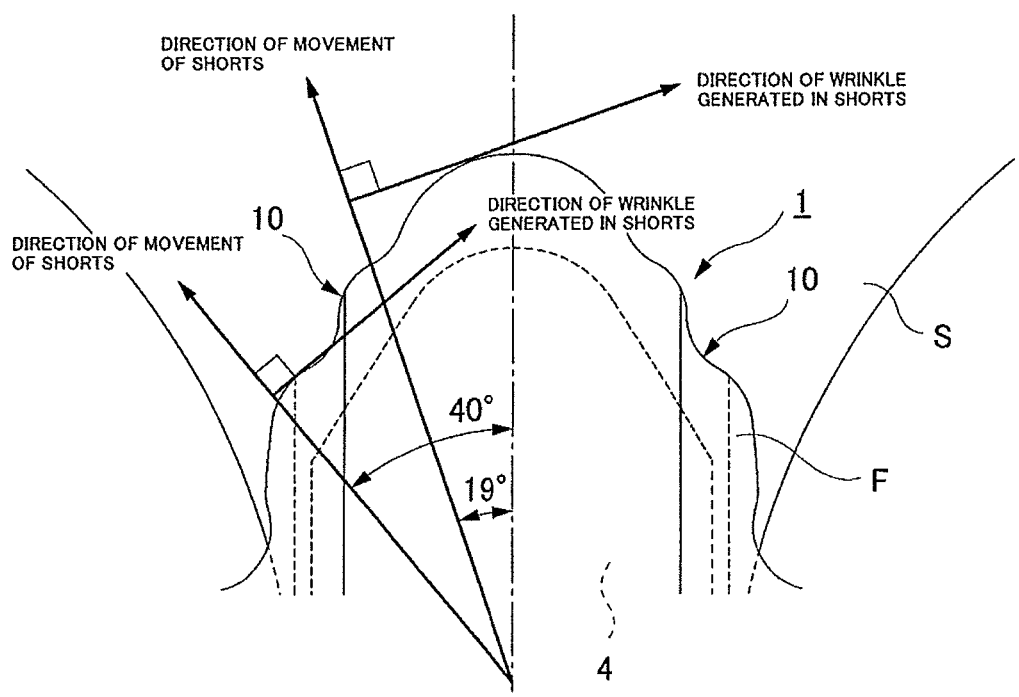
FIG. 6 is an enlarged view of the front side area of the sanitary napkin 1 in FIG. 5.

When the legs move backward and forward, for example, while walking, the shorts S expand or contract according to movement of the legs, and wrinkles are generated in the shorts S in the direction orthogonal to the direction of the movement of the legs. Specifically, it has been revealed from observation of the present inventors that, as shown in FIGS. 5 and 6, the direction in which the shorts S expand or contract according to movement of the legs while walking is approximately from 19 to 40°, approximately 36° on average, with respect to the center line in the longitudinal direction of the sanitary napkin 1. On this occasion, wrinkles tend to occur along the direction orthogonal to the movement of the shorts S, but, in the sanitary napkin 1 of the present invention, since the wave-like line 10 is formed in the front area and the back area, the wrinkle-generating force in the direction of the movement of the shorts S is gradually applied or is dissipated, preventing generation of wrinkles. In addition, in the convex curve 11, the convex curves 13, and the concave curves 12, since the direction of a line tangent to the outline is continuously changed, these curves can correspond to forces applied in various angles in a certain range.

Since the wave-like line 10 must allow the wrinkle-generating force to be gradually applied or to be dissipated, jagged lines are excluded from the present invention.

Other Embodiments (1) The pattern of the wave-like line 10 can be arbitrarily changed. That is, the curvatures of the convex curves 11 and 13 and the concave curves 12 forming the wave-like line 10 may be arbitrarily varied. For example, in the front area of the flap portion F, the curvature of the convex curve 11 formed at the front of the sanitary napkin 1 may be smaller than those of the convex curves 13 and the concave curves 12 formed along the inclining line 4a, and the curvatures of the convex curves and the concave curves in the front area may be different from those in the back area.

Figure 7A:
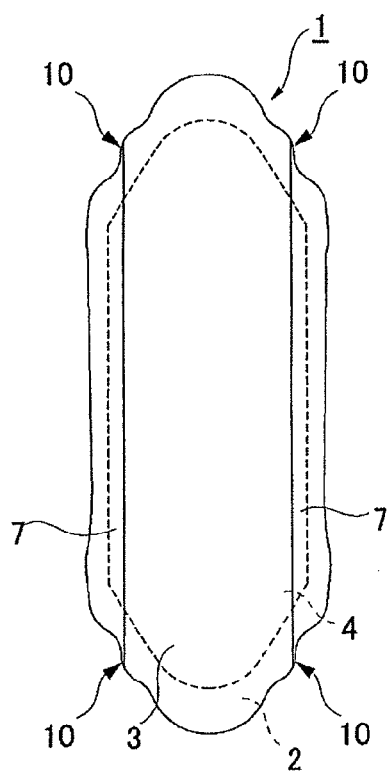
FIG. 7 is a development view of a sanitary napkin 1 showing another modification.
Figure 7B:
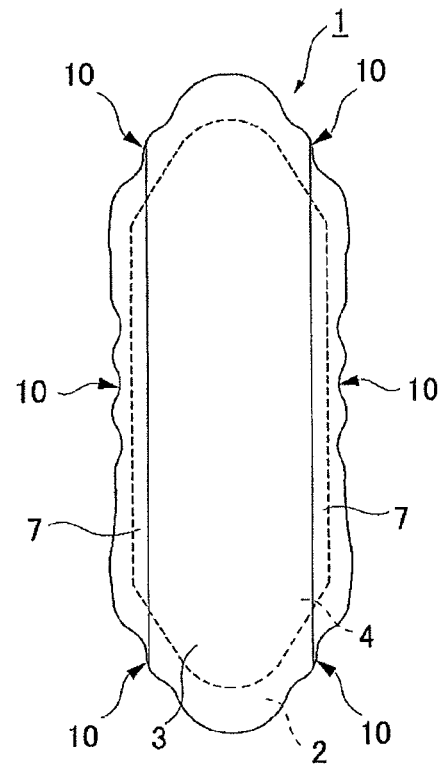
Figure 8:
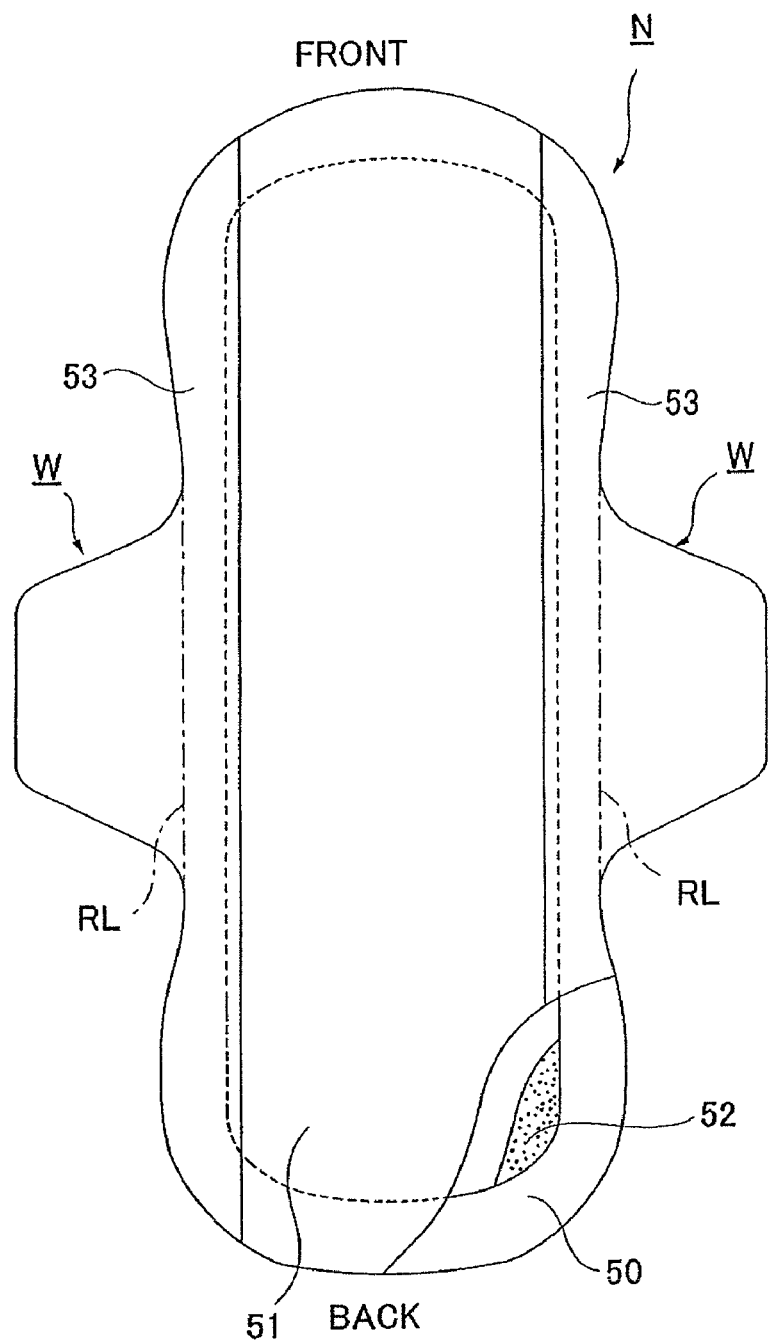
FIG. 8 is a partially broken development view of a conventional absorbent article N.
Figure 9:
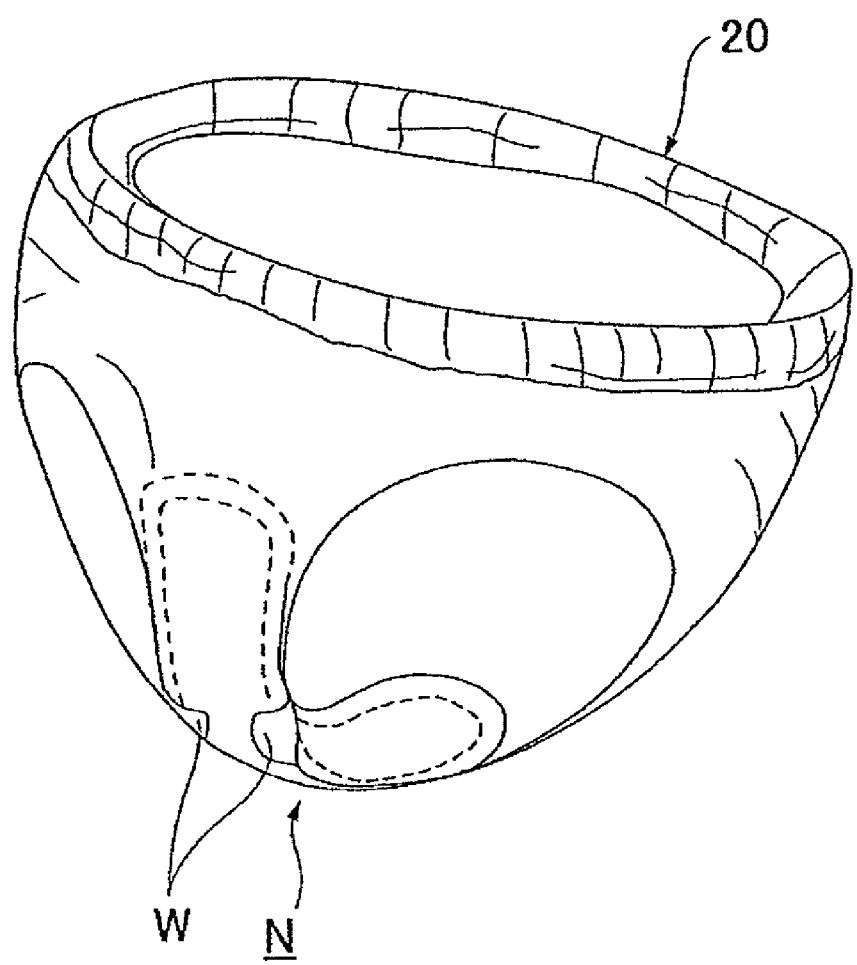
FIG. 9 is a perspective view showing the absorbent article N when it is worn.
Figure 10:
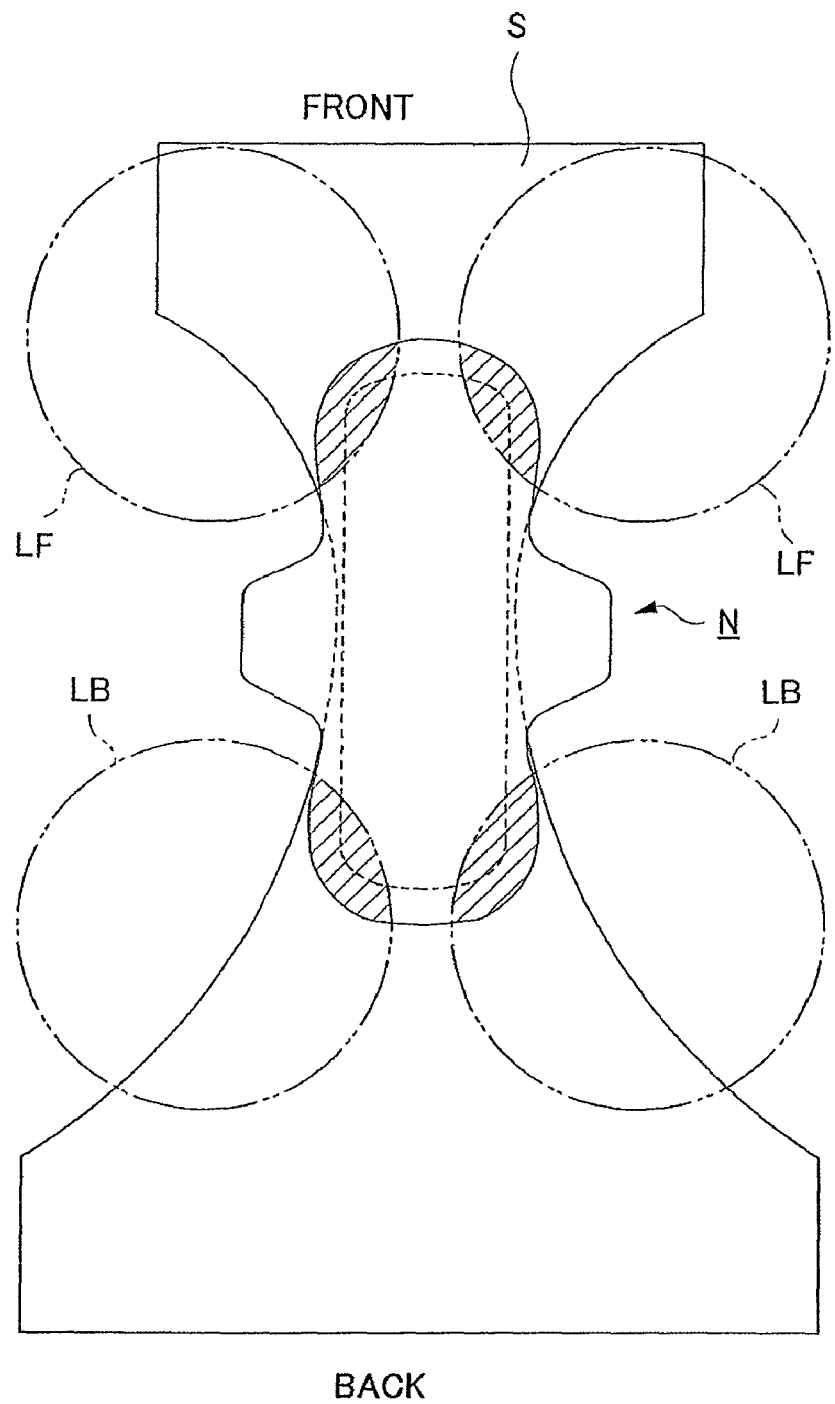
FIG. 10 is a development view of shorts showing positions of the legs with respect to the absorbent article N.

(2) In the above described embodiment, the sanitary napkin 1 has the wing-like flaps W, W on both sides, but the present invention can be also applied to those not having the wing-like flaps W, W, in the same way, as shown in FIG. 7(A). Furthermore, as shown in FIG. 7(B), in addition to the omission of the wing-like flaps W, W, the outer shape of the flap portion F on both sides may be the wave-like lines 10. Such a shape can correspond to wrinkles generated in the crotch portion as in the above-described embodiments.

The invention claimed is:

1. An absorbent article comprising a liquid-permeable top sheet, a liquid-impermeable back sheet, an absorber interposed therebetween, and a flap surrounding the absorber without including the absorber; and wherein the flap has a wave-like outline contour along each of a frontmost distal edge and a backmost distal edge;

wherein each said wavelike contour is composed of convex outline lengths and concave outline lengths and has a peripheral tangential line that continuously changes;

wherein at a front portion of the flap extending to the frontmost distal edge, flap width gradually narrows to form a frontmost distal convex curve portion, and wherein to each side of said frontmost distal convex curve portion are convex outline lengths and concave outline lengths of said frontmost distal edge wave-like outline contour; and wherein at a back portion of the flap extending to the backmost distal edge, flap width gradually narrows to form a backmost distal convex curve portion, and wherein to each side of said backmost distal convex curve portion are convex outline lengths and concave outline lengths of said backmost distal edge wave-like outline contour.

2. An absorbent article comprising a liquid-permeable top sheet, a liquid-impermeable back sheet, an absorber interposed therebetween, and a flap surrounding the absorber without including the absorber; and wherein the flap has an outer shape, at least in a front area and a back area of the absorbent article, of a wave-like line composed of convex curves and concave curves in which the direction of a line tangent to the outline of the flap is continuously changed; the width of the absorber gradually narrows in each of the front area and the back area in such a manner that lines incline toward each other to form a convex curve; and the wave-like line is formed along each of the inclining lines; and wherein the flap at each of the front area and the back area of the absorbent article is of a width from the edge of the absorber to the outline which is relatively large at central end extremities of the absorbent article and is relatively small adjacent the wave-like line formed along each of the inclining lines on both sides.

3. The absorbent article according to claim 2, wherein the flap portion in each of the front area and the back area of the absorbent article has an outer shape composed of a convex curve with a relatively large curvature at the central end extremities of the absorbent article and the wave-like line formed along each of the inclining lines on both sides being combination of concave curves and convex curves with relatively small curvatures.

4. An absorbent article comprising a liquid-permeable top sheet, a liquid-impermeable back sheet, an absorber interposed therebetween, and a flap surrounding the absorber without including the absorber; and wherein the flap has an outer shape, at least in a front area and a back area of the absorbent article, of a wave-like line composed of convex curves and concave curves in which the direction of a line tangent to the outline of the flap is continuously changed; the width of the absorber gradually narrows in each of the front area and the back area in such a manner that lines incline toward each other to form a convex curve; and the wave-like line is formed along each of the inclining lines; and wherein the flap portion in each of the front area and the back area of the absorbent article has an outer shape composed of a convex curve with a relatively large curvature at the central end extremities of the absorbent article and the wave-like line formed along each of the inclining lines on both sides being combination of concave curves and convex curves with relatively small curvatures.

* * * * *